(12) United States Patent
Kurtzman et al.

(10) Patent No.: US 9,382,566 B1
(45) Date of Patent: Jul. 5, 2016

(54) FERMENTATIVE PRODUCTION OF SOPHOROLIPIDS FROM SOYBEAN AND OTHER VEGETABLE OILS

(71) Applicant: The United States of America, as represented by the Secretary of Agriculture, Washington, DC (US)

(72) Inventors: Cletus P. Kurtzman, Peoria, IL (US); Neil P. Price, Edelstein, IL (US); Karen J. Ray, East Peoria, IL (US); Tsung Min Kuo, Ballston Lake, NY (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 71 days.

(21) Appl. No.: 14/041,786

(22) Filed: Sep. 30, 2013

Related U.S. Application Data

(63) Continuation of application No. 13/215,394, filed on Aug. 23, 2011, now abandoned.

(51) Int. Cl.
| | | |
|---|---|---|
| *C12P 19/44* | (2006.01) | |
| *C12R 1/72* | (2006.01) | |
| *C07H 15/10* | (2006.01) | |
| *C07H 15/06* | (2006.01) | |
| *C07H 15/04* | (2006.01) | |
| *C12R 1/22* | (2006.01) | |

(52) U.S. Cl.
CPC ............... *C12P 19/44* (2013.01); *C07H 15/04* (2013.01); *C07H 15/06* (2013.01); *C07H 15/10* (2013.01); *C12R 1/22* (2013.01); *C12R 1/72* (2013.01)

(58) Field of Classification Search
None
See application file for complete search history.

(56) References Cited

PUBLICATIONS

Price et al., "Structural characterization of novel sophorolipid biosurfactants from a newly identified species of Candida yeast" Carbohydrate Research (2012) vol. 348 pp. 33-41.*
Daniel et al., "Production of sophorolipids in high concentration from deproteinized whey and rapeseed oil in a two stage fed batch process using Candida bombicola ATCC 22214 and Cryptococcus curvatus ATCC 20509" Biotechnology Letters (1998) vol. 20 No. 12 pp. 1153-1156.*
Kurtzman et al., "Productionof sophorolipid biosurfactants by multiple species of the Starmerella (Candida) bombicola yeast clade" FEMS Microbiol Lett (2010) vol. 311 pp. 140-146.*
Konish I, Masaaki, et al., "Production of New Types of Sophorolipids by Candida batistae", Journal of Oleo Science, 57, (6), 2008, pp. 359-369.
Rosa, Carlos A., et al., "Candida batistae, a new yeast species associated with solitary digger nesting bees in Brazil", Mycologia, 91(3), 1999, pp. 428-433.

* cited by examiner

*Primary Examiner* — Eric Olson
(74) *Attorney, Agent, or Firm* — John D. Fado; Gail E. Poulos

(57) ABSTRACT

Open chain sophorolipids may be produced by fermentation with *Candida* sp. NRRL Y-27208 or *C. riodocensis*. Dimers and trimers of sophorolipids are also produced. The sophorolipds are produced by inoculating a fermentation medium comprising a carbon source and a lipid, with *Candida riodocensis* or *Candida* species NRRL Y-27208, and incubating under aerobic conditions and for a period of time effective to produce an open chain sophorolipid in the medium. The sophorolipids may be subsequently recovered from the fermentation medium.

13 Claims, 9 Drawing Sheets

Sophorolipid Biosurfactants from a Newly identified species of the *Starmerella* yeast clade.

Lactone Type · Newly Identified Free Acid Type · Free Acid Type

A · B · C

FERMENTATIVE PRODUCTION OF SOPHOROLIPIDS FROM SOYBEAN AND OTHER VEGETABLE OILS

BACKGROUND OF THE INVENTION

1. Field of the Invention

The invention relates to a method for producing open-chain sophorolipids by fermentation with a yeast.

2. Description of the Prior Art

Biosurfactants are microbially produced, renewable, surface-active compounds that are increasingly being used for oil and mineral recovery, and in detergents, cosmetics, and anti-microbial formulations (Georgiou et al. Nature Biotechnol. 1992. 10:60-65; Cooper and Zajic. Adv. Appl. Microbiol. 1980. 26:229-253; Dembitsky Lipids. 2004. 39:933-953; and Banat et al. R. Appl. Microbiol. Biotechnol. 2010. 87:427-444). The annual worldwide production of surfactants is currently about 10 million tons, and are mostly derived from petroleum feedstocks, but production from renewable sources is now of great interest Banat et al., ibid). Included in the glycolipid-type biosurfactants are sophorolipids from various *Starmerella* yeast species (Van Bogaert et al. 2011. Process Biochem. 46:821-833; Rau et al. 2001. Ind. Crops Prod. 13:85-92; Develter and Lauryssen. 2010. Eur. J. Lipid Sci. Technol. 112:628-638; and Baccile et al. 2010. Green Chem. 12:1564-1567), which consist of the disaccharide sophorose linked to a long chain hydroxy fatty acid. Among yeasts of the *Starmerella* clade (genetically related group of species) that have been examined, the greatest yield of sophorolipids has been reported from *Candida apicola* and *Starmerella bombicola* (Van Bogaert et al. 2007 Appl. Microbiol. Biotechnol. 76:23-34). These sophorolipids are a partially acetylated 2-O-β-D-glucopyranosyl-D-glucopyranose unit attached β-glycosidically to 17-L-hydroxyoctadecanoic or 17-L-hydroxy-Δ9-octadecenoic acid (Tulloch et al. 1962. Can. J. Chem. 40:1326-1338; and Tulloch et al. 1968. Can. J. Chem. 46:345-348) and can be acetylated on the 6'- and/or 6"-positions. The hydroxy fatty acid is generally 16 or 18 carbon atoms, and may contain one or more unsaturated bonds (Asmer et al. 1988. J. Am. Oil Chem. Soc. 65:1460-1466; and Davila et al. 1993. J. Chromatogr. 648:139-149). The fatty acid carboxyl group is either free (acidic or open form) or internally esterified at the 4"-position (lactone form). The 1,4"-lactone form of the sophorolipids are nonionic surfactants with a critical micelle concentration (CMC) of 40-100 µg·mL$^{-1}$ and are reported to lower the surface tension of water by 30-40 mN·m$^{-1}$, making them especially useful as emulsifiers for oil/water mixtures (Van Bogaert et al. 2007. ibid).

Interest in sophorolipids is not limited to production of surfactants. The unique chemical structure of sophorolipids can serve as the basis for synthesizing certain hydroxy fatty acids and other compounds (Van Bogaert et al. 2007. ibid). Perhaps of greater interest are reports that these glycolipids have antimicrobial activity against certain yeasts (Ito et al. 1980. Agric Biol Chem. 44:2221-2223), plant pathogenic fungi (Yoo et al. 2005. J Microbiol Biotechnol. 15:1164-1169) and bacteria (Mager et al. 1987. European Patent no. 0209783; and Lang et al. 1989. Fett Wiss Technol Fat Sci Technol. 91:363-366). Furthermore, Shah et al. (2005. Antimicrob Agents Chemother. 49:4093-4100) showed inhibition of the HIV virus by sophorolipids, and Chen et al. (2006. Enzyme Microb Technol. 39:501-506) provided evidence that the compounds have anti-cancer activity.

As noted above, sophorolipids are synthesized by a phylogenetically diverse group of yeasts. The earliest report appears to be that of Gorin et al. (1961. Can J Chem. 39:846-855), who demonstrated sophorolipid biosynthesis by the anamorphic ascomycetous yeast *Candida apicola*, which was initially identified as *C. magnoliae*. Later, Spencer et al. (1970. Antonie van Leeuwenhoek. 36:129-133) showed sophorolipid production by *C. bombicola*, and Konoshi et al. (2008. J Oleo Sci. 57:359-369) reported *C. batistae* to also form sophorolipids. The preceding three *Candida* species are closely related, but sophorolipid biosynthesis was also demonstrated for the less closely related *Wickerhamiella domercqiae* (Chen et al., 2006. ibid) as well as for the basidiomycetous yeast *Rhodotorula bogoriensis* (Tulloch et al. 1968. ibid).

Phylogenetic analysis of sequences for the D1/D2 domains of the nuclear large subunit ribosomal RNA gene has shown that *C. apicola* and *C. bombicola* are members of a clade that is well separated from other ascomycetous yeasts (Kurtzman & Robnett. 1998. Antonie van Leeuwenhoek. 73:331-371). *Candida bombicola* is the first member of the clade for which ascospore formation was discovered and the species was reassigned to the teleomorphic genus *Starmerella* (Rosa & Lachance. 1998. Int J Syst Bacteriol. 48:1413-1417). With the application of sequence analysis to yeast identification, the group of yeasts related to *S. bombicola*, now termed the *Starmerella* clade, has increased markedly in the past decade to over 40 species with many not yet described and presently recognized only from their gene sequences, which have been deposited in GenBank. *Candida apicola, C. batistae* and *S. bombicola* are the only members of the *Starmerella* clade that have been reported to produce sophorolipids.

The *S. bombicola* sophorolipids are nearly identical to those of *C. apicola* (Spencer et al. 1970. ibid). Chen et al. (2006. ibid) observed more than six sophorolipids from *Wickerhamiella domericqiae*, and identified one as 17-L-(-oxy)-octadecanoic acid 1,4"-lactone 6',6"-diacetate, that is also the major sophorolipid from *C. apicola* and *C. bombicola*. Tulloch et al. (1968. ibid) also discovered similar sophorolipids from *C. bogoriensis*, but that differ in the hydroxy fatty acid moiety, which in this instance is 13-hydroxydocosanoic acid (J. Biol Chem. 1979. 254:1944-1950).

However, despite these and other advances, the need remains for improved sophorolipids and methods for their production.

SUMMARY OF THE INVENTION

We have now discovered that sophorolipids may be produced by fermentation with *Candida* sp. NRRL Y-27208 or *Candida riodocensis*, which have not been previously known to produce these compounds. Moreover, in contrast with most other previously reported yeasts of the *Starmerella* clade, the *Candida* sp. NRRL Y-27208 and *C. riodocensis* produce very little of the lactone form of sophorolipid; rather, the major sophorolipid for these two species is an open-chain (i.e., free acid) form. Further still, we have also discovered that these two yeasts, as well as *C. stellata*, produce dimers and trimers of sophorolipids which have not been reported previously.

The sophorolipids are produced by inoculating a fermentation medium comprising a carbon source and a lipid, with *C. riodocensis* or *Candida* species NRRL Y-27208, and incubating under aerobic conditions and for a period of time effective to produce an open chain sophorolipid in the medium. The sophorolipids may be subsequently recovered from the fermentation medium.

In accordance with this discovery, it is an object of this invention to provide a fermentative method for the production of open chain or free acid forms of sophorolipids.

Another object of this invention is to provide a method for the fermentative production of open chain sophorolipids in high yields from a variety of carbon sources and lipids, including triglycerides.

A further object of this invention is to provide a method for the fermentative production dimers and trimers of sophorolipids.

Other objects and advantages of the invention will become readily apparent from the ensuing description.

DETAILED DESCRIPTION OF THE INVENTION

Figure 1:
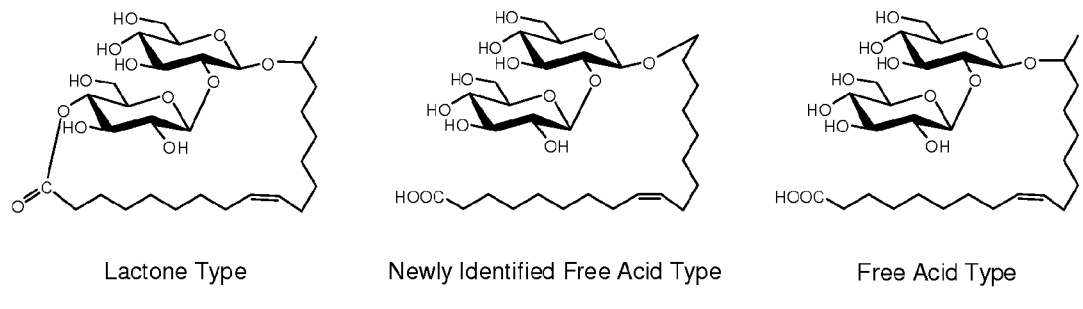
FIG. 1 shows a structural characterization of different sophorolipids produced by yeasts of the *Starmerella* clade (with the fatty acid moiety shown as oleic acid for purposes of illustration). The lactone type which is produced by *C. bombicola* is shown at (a). *C. bombicola* also produces a small amount of free acid type sophorolipid characterized by an ω-1 hydroxyl acyl group shown at (c). *Candida* sp. NRRL Y-27208 and *C. riodocensis* produce a free acid type sophorolipid characterized by an co hydroxyl acyl group shown at (b).

Sophorolipids are produced in accordance with this invention by fermentation with either *Candida* sp. NRRL Y-27208 or strains of *Candida riodocensis*, although use of *Candida* sp. NRRL Y-27208 is preferred. *Candida* sp. NRRL y-27208 is available from the general collection of the Agricultural Research Service Culture Collection under this same accession number, NRRL Y-27208, and was also deposited at the Centraalbureau voor Schimmelcultures (CBS) in the Netherlands as *Candida bombicola* deposit accession number CBS 7267. This same strain *Candida* sp. NRRL Y-27208 has been deposited under the provisions of the Budapest Treaty in the Agricultural Research Service Culture Collection in Peoria, Ill., on Nov. 24, 2015 and has been assigned deposit accession number NRRL Y-67153. Further, the subject deposit will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the strain. The depositor acknowledges the duty to replace the deposits should the depository be unable to furnish a sample when requested, due to the condition of the deposits. All restrictions on the availability to the public of the subject deposit will be irrevocably removed upon the granting of a patent disclosing it. It is understood that this invention may also be practiced using this same strain from these other deposit accessions with the same results.

Although *Candida* sp. NRRL Y-27208 was previously identified as a strain of *Candida bombicola*, we have determined that the strain is in fact a new *Candida* species based on D1/D2 LSU rRNA gene analysis. Moreover, as described in the examples hereinbelow, *Candida* sp. NRRL Y-27208 produces significantly different sophorolipids than *C. bombicola*. The cultural and biochemical characteristics of *Candida sp. NRRL Y-27208 are substantially the same as provided in the description of the CBS 7267 accession and are set forth below. The strain grows at 25-30° C. on GPYA solid culture medium, but does not grow at or above 35° C. Under anaerobic conditions, the strain ferments glucose or sucrose, but does not ferment any of galactose, maltose, Me α-D-glucoside, a,a-trehalose, melibiose, lactose, cellobiose, melezitose, raffinose, inulin or starch. A variety of carbon sources are assimilated, including glucose, galactose, L-sorbose, D-ribose, D-xylose, sucrose, salicin, arbutin, raffinose, glycerol, erythritol, xylitol, D-glucitol, D-mannitol, D-glucono-1,5-lactone, D-gluconate, and citrate. However, D-glucosamine, L-arabinose, D-arabinose, L-rhamnose, maltose, α,α-trehalose, Me α-D-glucoside, cellobiose, melibiose, lactose, melezitose, inulin, starch, ribitol, L-arabinitol, galactitol, myo-inositol, 2-keto-D-gluconate, acetic acid, D-glucuronate, D-galacturonate, DL-lactate, succinate, propane-1,2-diol, butane-2,3-diol, quinic acid, D-glucarate, and D-galactonate are not assimilated. Nitrogen sources which are utilized include ammonium salts, ethylamine and lysine, although the strain does not utilize nitrate or nitrite. The strain does not form starch or hydrolyze urea.

The yeast *Candida riodocensis* which may also be used in this invention was originally described by Pimentel et al. (2005. *Candida riodocensis* and *Candida cellae*, two new yeast species from the *Starmerella* clade associated with solitary bees in the Atlantic Rain Forest of Brazil. FEMS Yeast Res. 5:875-879). The morphological, cultural and biochemical characteristics of *C. riodocensis* are substantially the same as described in Pimental et al. above, and by Lachance et al. (The Yeasts, A Taxonomic Study, 5$^{th}$ edn. Elsevier Science Publishers. 2011), the contents of each of which are incorporated by reference herein. In review, morphologically, cells of *C. riodocensis* grown in 0.5% yeast extract, 2% glucose broth at 25° C. after 3 days are ovoid to ellipsoidal and reproduce by multilateral budding. The yeast strain grows at 37° C., but does not grow at or above 40° C. Under anaerobic conditions, the strain ferments glucose, but does not ferment any of galactose, sucrose, maltose, trehalose, lactose, or raffinose. A variety of carbon sources are assimilated, including glucose, galactose, L-sorbose, glycerol, D-mannitol and D-glucitol. However, inulin, sucrose, raffinose, melibiose, lactose, trehalose, maltose, melezitose, starch, L-rhamnose, D-xylose, D or L-arabinose, D-ribose, methanol, erythritol, ribitol, galactitol, myo-inositol, DL-lactate, succinate, citrate, D-gluconate, D-glucosamine, N-acetyl-D-glucosamine, and hexadecane are not assimilated. Nitrogen sources utilized include ammonium salts, ethylamine and lysine, although the strain does not utilize nitrate or nitrite. The strain does not form starch or hydrolyze urea.

Production of sophorolipids may be accomplished by culture of the aforementioned *Candida* sp. NRRL Y-27208 or strains of *Candida riodocensis*, using conventional techniques under aerobic conditions that are effective to promote growth and sophorolipid production. The fermentation is preferably conducted as a batch process, with agitation, although it may also be conducted as a fed-batch or continuous process. Any number of well-known liquid or solid culture media may be used, although growth on aqueous liquid media is preferred as the sophorolipid is secreted into the media and recovery is simplified. A suitable medium will contain a utilizable source of carbon and a lipid which are effective to support growth of *Candida* species NRRL Y-27208 or *C. riodocensis* and their production of sophorolipid. The sophorolipids of this invention may be produced from a wide variety of lipids and carbon sources. The medium will also preferably include an organic or inorganic nitrogen source such as from protein, amino acids, yeast extract, yeast autolysates, ammonia or preferably ammonium salts, as well as elements such as potassium, magnesium, calcium, zinc and manganese, preferably as salts, phosphorous such as from phosphates, and other growth stimulating components. By way of example, although prepared commercially available media (supplemented with lipids) may be used, such as glucose-yeast extract-peptone water, Trypticase-soy broth, and Potato dextrose broth, the use of a defined medium such as described in the Examples is preferred. Each of the various components should be present in concentrations effective to promote growth of the yeast and sophorolipid production, and may be readily determined by the producer.

A variety of carbon sources will support growth of *Candida* species NRRL Y-27208 and *C. riodocensis* and the production of sophorolipid thereby, and are suitable for use in the fermentation medium herein. The C source utilized may vary with the particular yeast selected (i.e., *Candida* sp. NRRL Y-27208 or strains of *Candida riodocensis*) as noted above. Thus, suitable C sources include, but are not limited to, one or more of glucose, xylose, mannose, sucrose, galactose, mannitol, sorbose, ribose, salicin, arbutin, raffinose, glycerol, erythritol, xylitol, D-glucitol, D-mannitol, D-glucono-1,5-lactone, gluconate, citrate, molasses, hydrolyzed starch, hydrolyzed cellulosic material comprising glucose, corn syrup, beet syrup, sugar cane syrup, sulfite waste liquor (includes xylose), or combinations thereof. Of these, glucose, xylose, mannose, galactose, mannitol, hydrolyzed starch, and hydrolyzed cellulosic material comprising glucose are preferred. Interestingly, the C source will not affect the structure of the sophorolipid produced. As noted in the examples, the sugar composition of the sophorose moiety is consistent regardless of the carbon source (carbohydrate) used.

A variety of lipids are also suitable for use in the fermentation medium and include oils or fats (including those of plant or animal origin) which contain free fatty acids or their salts or their esters, including triglycerides. Potential fatty acids (or their triglycerides) which can be used as the starting material, include those with different chain lengths (i.e., number of $CH_2$ groups), or saturated or unsaturated fatty acids (i.e., those with or without carbon/carbon double bonds). The sophorolipid produced by the fermentation, specifically the fatty acid moiety linked to the sophorose, may vary with the particular lipid selected. Thus, it is possible to produce a broad variety of sophorolipids with potentially different properties (longer chain length detergents generally have improved surfactant properties). Thus, suitable fatty acids include fatty acids of the formula $R_2$—$COOR_x$ wherein $R_2$ is a saturated or unsaturated, straight or branched chain hydrocarbon, and $R_x$ is H or an alkali metal, branched or straight chain alkyl or alkenyl groups, aromatic containing groups, or glycerides (mono-, di- or triglyceride). It is also recognized that the $R_2$ moiety encompasses hydrocarbons which may be optionally substituted. Preferred fatty acids include, but are not limited to free and esterified fatty acids containing from 16 to 18 carbon atoms, particularly oleic, stearic and palmitic acid.

As starting materials in the fermentation of the invention, the fatty acids may be provided in substantially pure form or, in the alternative, they may be provided as a mixture or in impure form. Moreover, although the fatty acids may be free acids, the fermentation may also be conducted using fatty acids which are esterified with aliphatic alcohols such as methanol, ethanol, isopropanol, or branched chain alcohols such as 2-ethyl hexanol or Guerbet alcohols, or with glycerol as mono-, di- or triglycerides. In a particularly preferred embodiment, because fatty acids occur predominantly as triglycerides in plant oils, naturally occurring oils may be used directly in the fermentation, thereby foregoing the need for any preliminary fatty acid isolation of the oil. By way of example and without being limited thereto, suitable oils include soybean, cottonseed, corn, olive, peanut, palm, sesame, sunflower, canola, castor, safflower, linseed, oiticica, tung, rice, crambe, rape, and canola oils, with corn oil, soybean oil and olive oil being particularly preferred.

The practitioner skilled in the art will of course recognize that for products requiring a high degree of purity or uniformity, the oils may first be hydrolyzed to obtain free fatty acids for use as starting materials in the fermentation. Hydrolysis of the oils to the fatty acids may be achieved using conventional splitting techniques or alkali splitting of fats. Suitable alkali splitting techniques include, for example, treatment with sodium methoxide, or sodium or potassium hydroxide [see "A.O.C.S. Tentative Method Ca 6b-53", in: Official and Tentative Methods of the American Oil Chemist's Society, third edition, AOCS, Chicago, Ill., (1973)]. Other conventional techniques including splitting with steam under pressure are also effective.

The temperature and pH of the fermentation are not critical, although it is understood that they should be suitable for growth of the yeast. The disclosed *Candida* species NRRL Y-27208 and *C. riodocensis* strains will grow and produce sophorolipids over relatively wide pH and temperature ranges, generally a temperature between about 25 to less than 35° C., or 25 to 37° C., respectively, preferably between about 25 to 30° C., and a pH between about 3 to 5, preferably between about 3.5 to 4.5. Neutralization of the acid produced during the fermentation is optional but preferred. For example, the pH of the medium at the commencement of the fermentation is preferably in the range of about 4.5 and is controlled by addition of base to a pH of about 3.5 as the fermentation progresses. Control or maintenance of the pH in the course of the fermentation may be accomplished using manual or automatic techniques conventional in the art, such as using automatic pH controllers for adding base. Preferred bases employed for pH control include but are not limited to NaOH and KOH.

Under these cultivation conditions, optimal production of sophorolipids is achieved between about 56 to about 168 hours. Upon completion of the fermentation, the sophorolipids may be isolated or separated from the yeast cells using techniques conventional in the art, such as by centrifugation or filtration.

At the completion of the fermentation, accumulated sophorolipids may be recovered from the fermentation broth using conventional techniques. Although formulations of the sophorolipids may be prepared directly from liquid culture medium from which cells have been removed in the above-described manner, as a practical matter, it is envisioned that commercial formulations of the sophorolipids will require concentration and preferably substantial purification. Purification is particularly preferred for applications demanding a high degree of purity where contamination by enzymes, microbial products, or culture media components may be undesirable. Without being limited thereto, the preferred recovery technique includes initial acidification to approximately pH 2, followed by solvent extraction with ethyl acetate to remove sophorolipids and unused lipid. Following solvent removal by evaporation, remaining lipids may be separated from the sophorolipid product by washing in hexane, wherein the lipid accumulates in the hexane fraction leaving a substantially pure solid sophorolipid fraction. If desired further purification and separation of different sophorolipids may be effected, for example, by size exclusion chromatography.

In contrast with most other previously reported yeasts of the *Starmerella* clade, the *Candida* sp. NRRL Y-27208 and *C. riodocensis* produce very little of the lactone form of sophorolipid. Instead, the major sophorolipid produced by these two species is not a lactone but a free acid or open chain form. Thus, the acyl carboxyl tail of the fatty acid moiety of the sophorolipid is not esterified to a glucose of the sophorose moiety (as in the lactone form), but remains as a free acid. Furthermore, the *Candida* sp. NRRL Y-27208 and *C. riodocensis* produce sophorolipids wherein the sophorose moiety is β-O-glycosidically linked to the terminal (ω) carbon of the fatty acid hydrocarbon tail, rather than at the penultimate (ω-1) carbon of the fatty acid tail as is common on most other sophorolipids. The structural differences between the various sophorolipids are illustrated in FIG. 1 showing sophorolipids produced from oleic acid. The lactone form of the sophorolipid, which is typically the predominant form produced by other known yeasts, is shown at (a) in the Figure, while two free acid forms, differing at the linkage site of the sophorose moiety to the fatty acid tail, are shown at (b) and (c). The sophorolipid produced by *Candida* sp. NRRL Y-27208 and *C. riodocensis* wherein the fatty acid moiety is linked to the sophorose moiety at the terminal (ω) carbon of the fatty acid hydrocarbon tail are shown at (b). The minor free acid type of sophorolipid produced by *C. bombicola* wherein the fatty acid moiety is linked to the sophorose moiety at the penultimate (ω-1) carbon of the fatty acid tail is shown at (c).

The sophorolipids which are produced by the fermentation with *Candida* sp. NRRL Y-27208 or *C. riodocensis* herein may be acetylated at one or both of the 6' or 6" hydroxyls of the sophorose moiety. Typically, a major proportion of the sophorolipids are produced in a di-O-acetyl free acid form, with smaller amounts of mono-O-acetyl and non-acetyl sophorolipids being formed.

In addition, we have also discovered that *Candida* sp. NRRL Y-27208 and *C. riodocensis* produce dimers and trimers of sophorolipids. The predominant sophorolipid produced by *Candida* sp. NRRL Y-27208 and *C. riodocensis* may be represented by the formula:

$$R_1-O-R_2-COOH \qquad (1)$$

wherein $R_1$ is a 1'-linked sophorose moiety and $R_2$ comprises a hydrocarbon (i.e., fatty acid hydrocarbon tail) which may be straight or branched or saturated or unsaturated. In accordance with this formula, the 1'-linked sophorose moiety $R_1$ would be of the formula (2):

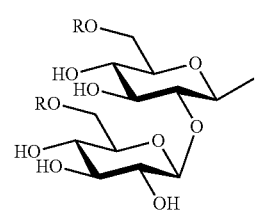

wherein R at the 6' and 6" positions of the sophorose are independently selected from H or acetyl. In a preferred embodiment wherein the lipid is selected from oleic acid or its salts or esters (including mono-, di- or triglycerides), stearic acid or its salts or esters, and palmitic acid or its salts or esters, $R_2$ is a C17 straight chain hydrocarbon comprising a 9,10 double bond, a C17 saturated, straight chain hydrocarbon, and a C15 saturated, straight chain hydrocarbon, respectively.

The dimers and trimers which are produced by the yeasts of this invention may be represented by the formula:

$$R_1[-O-R_2-C(O)-R_3]_n-O-R_2-C(O)-R_4 \quad (3)$$

wherein n is 1 or 2, $R_1$ is a 1'-linked sophorose moiety, $R_3$ is a 1',4"-linked sophorose moiety, $R_4$ is an OH or a 4"-linked sophorose moiety and $R_2$ comprises a hydrocarbon which may be straight or branched or saturated or unsaturated. In this formula, 1',4"-linked sophorose moiety, $R_3$ would be of the formula (4):

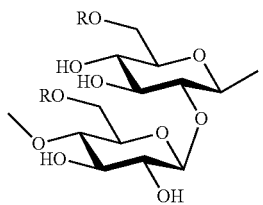

and the 4"-linked sophorose moiety of $R_4$ would be of the formula (5):

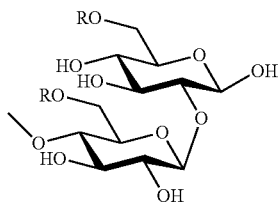

wherein R is as described above.

The open chain sophorolipids produced in accordance with this invention may be used as surfactants in a variety of applications including, but not limited to oil and mineral recovery, detergents, cosmetics, and anti-microbial formulations. It is also envisioned that the sophorolipids may have utility as antimicrobial agents with activity against one or more yeasts, plant pathogenic fungi, and bacteria.

The following examples are intended only to further illustrate the invention and are not intended to limit the scope of the subject matter which is defined by the claims.

Example 1

In this example, described in our publication of Kurtzman et al. (2010. FEMS Microbiol. Lett. 311:140-146, the contents of which are incorporated by reference herein) we examined species of the *Starmerella* clade for production of sophorolipids using a MALDI-TOF MS based screen similar to that used previously to identify bacterial biosurfactants, rhamnolipids, surfactins, and iturins (Price et al. 2007. FEMS Microbiol. Lett. 271:83-89; Rooney et al. 2009. FEMS Microbiol. Lett. 295:82-87). From this analysis, we found three additional sophorolipid producing species of the *Starmerella* clade, one of which is a novel species, and have determined that two forms of sophorolipids are selectively synthesized by different species within the clade.

Materials and Methods

Yeast Cultures

The strains examined in this study were obtained from the ARS Culture Collection (NRRL), National Center for Agricultural Utilization Research, Peoria, Ill., USA, and maintained on YM agar (3 gL$^{-1}$ yeast extract, 3 gL$^{-1}$ malt extract, 5 gL$^{-1}$ peptone, 10 gL$^{-1}$ glucose, 20 gL$^{-1}$ agar, in distilled water).

Sophorolipid Production Medium and Growth Conditions

The medium used for production of sophorolipids was termed SL medium and composed of 100 gL$^{-1}$ glucose, 87.5 gL$^{-1}$ (100 mL$^{-1}$) oleic acid (Aldrich, technical grade), 1.5 gL$^{-1}$ yeast extract, 4 gL$^{-1}$ NH$_4$Cl, 1 gL$^{-1}$ KH$_2$PO$_4$.H$_2$O, 0.1 gL$^{-1}$ NaCl and 0.5 gL$^{-1}$ MgSO$_4$.7H$_2$O, in distilled water. The initial pH was adjusted to 4.5 with 6N KOH. Unless otherwise specified, cultures were grown at 25° C. in 50 mL Erlenmeyer flasks with 10 mL of SL medium and shaken at 200 rpm in an Innova 4335 shaker incubator. Incubation times were up to 168 h and the time is given with each reported experiment. The pH of the flask cultures was adjusted to 3.5 twice daily by the addition of 1N NaOH.

Separation and Quantitation of Sophorolipids and Oleic Acid

The 10 mL of spent SL medium from each shake flask was acidified with 0.4 mL 6N HCl and extracted twice with 40 mL of ethyl acetate to remove sophorolipids and unmetabolized oleic acid. The ethyl acetate extract was reduced to dryness in a rotoevaporator, redissolved in 2 mL chloroform, transferred to a glass vial and reduced to dryness under a nitrogen gas stream. Oleic acid was separated from sophorolipids in the mixture by three separate 3 mL hexane extractions. The hexane was evaporated and the concentration of oleic acid was quantified by weight, which was confirmed by gas-liquid chromatography (Price et al. 2009. Carbohyd. Res. 344:204-209). The residue that remained after hexane extraction was the sophorolipid fraction and the amount was determined by weight following confirmation of the presence of sophorolipids by MALDI-TOF mass spectrometry as described below. Yields of sophorolipids and consumption of oleic acid are reported as averages and were determined from duplicate cultures, which varied no more than 11%.

MALDI-TOF Mass Spectrometric Screen for Sophorolipids

Matrix assisted laser desorption/ionization mass spectrometry (MALDI-MS) screening was accomplished using a Bruker Omniflex instrument in reflectron mode with positive ion detection. The samples were dissolved in ethyl acetate and the matrix used was 2,5-dihydroxybenzoic acid. The instrument conditions were used as described previously (Price et al. 2009. ibid). Determinations were made in duplicate.

DNA Preparation, Gene Sequencing and Phylogenetic Analysis

The methods used for DNA isolation, purification and sequencing were reported earlier (Kurtzman & Robnett. 1998. ibid). DNA characterization was initiated by PCR amplification of the D1/D2 domain of the large subunit rRNA gene followed by sequencing reactions using the ABI Big Dye Terminator v3.0 Cycle Sequencing Kit. Sequences of both DNA strands were determined by capillary electrophoresis using an ABI 3130 genetic analyzer (Applied Biosystems, Foster city, CA). Phylogenetic analysis of the gene sequences was determined with the maximum parsimony program included in PAUP*4.063a (Swofford. 1998. PAUP*4.0: Phylogenetic Analysis Using Parsimony. Sinauer Associates. Sunderland, Mass.). Sequences were visually aligned for analysis and *Saccharomyces cerevisiae* was the designated outgroup species.

Results and Discussion

In the present example, 26 strains representing 19 species of the *Starmerella* clade were analyzed for production of sophorolipids. Five of the 19 species tested showed significant production of sophorolipids: *C. apicola, S. bombicola, C. riodocensis, C. stellata* and a new species of *Candida*, NRRL Y-27208, which will be described in a future study. In our earlier work, phylogenetic analysis detected 12 species in the *Starmerella* clade (Kurtzman & Robnett. 1998. ibid) and they separated into two subclades, one represented by *C. bombicola* and the other by *C. magnoliae*. With the widespread application of gene sequence analysis in yeast taxonomy, 41 separate lineages (species) are known for the clade and all were included in the phylogenetic analysis 1 to give perspective to placement of species that were tested for biosynthesis of sophorolipids. However, many of the lineages are undescribed species that are recognized only from their gene sequences, and cultures are not presently available for analysis.

Even with addition of many new lineages to the *Starmerella* clade, the two subclades originally recognized are still evident. Based on the present analysis, sophorolipids are produced only by members of the *S. bombicola* subclade. Although not included in our analysis, *C. batistae*, a member of this subclade, was shown by Konoshi et al. (2008. ibid) to form sophorolipids. However, not all members of the subclade produce sophorolipids and for *C. apicola*, NRRL Y-2481 gave the greatest yield of any strain tested (52.7 g/L), whereas NRRL Y-6688, a somewhat divergent strain of this species, produced essentially no sophorolipids. In earlier studies of sophorolipid biosynthesis by *C. apicola*, Tulloch et al. (1968. ibid) reported a yield of 40 gL$^{-1}$ without optimizing the culture medium, much as we found in our assays. Our goal in this study was to test previously unexamined species for sophorolipid production without optimization. The effect of incubation time, shaker speed and glucose concentration on sophorolipid production by *C. bombicola* NRRL Y-17069 and *Candida* sp. NRRL Y-27208, which as described below, produce sophorolipids with a different molecular structure.

*Starmerella bombicola* NRRL Y-17069 gave maximum sophorolipid yield after 144 h incubation (48.9 g/L), whereas *Candida* sp. NRRL Y-27208 was near maximum yield after 168 h (20.1 g/L), the time of the final analysis (Table 1). For both species, increasing yields of sophorolipids were accompanied by decreasing concentrations of oleic acid, which was expected because of incorporation of oleic acid into the sophorolipid molecule. The requirement for high aeration in production of sophorolipids was reported earlier (Guilmanov et al. 2002. Biotechnol. Bioeng. 77:489-494) and again shown in this study for both *S. bombicola* NRRL Y-17069 and *Candida* sp. NRRL Y-27208 (Table 2). Maximum yield of sophorolipids was reached at a shaker speed of 350 rpm.

Glucose concentration noticeably affected sophorolipid production by both *S. bombicola* NRRL Y-17069 and *Candida* sp. NRRL Y-27208 (Table 2). For *S. bombicola*, 50 gL$^{-1}$ glucose gave 48.8 gL$^{-1}$ sophorolipid, whereas 150 gL$^{-1}$ glucose yielded 95.4 gL$^{-1}$ sophorolipid. The increased sophorolipid production was not fully reflected in the reduced concentration of residual oleic acid (Table 2), suggesting that a portion of the lipid moiety was synthesized by the yeast. During production of sophorolipids, the pH of the culture medium dropped from 4.5 to as low as 1.8. To sustain production, the pH was readjusted twice daily to 3.5 with 1N NaOH. The precipitous decrease in pH during sophorolipid production and its impact on reducing yield was reported earlier by Gobbert et al. (1984. Biotechnol. Lett. 6:225-230).

Figure 2:
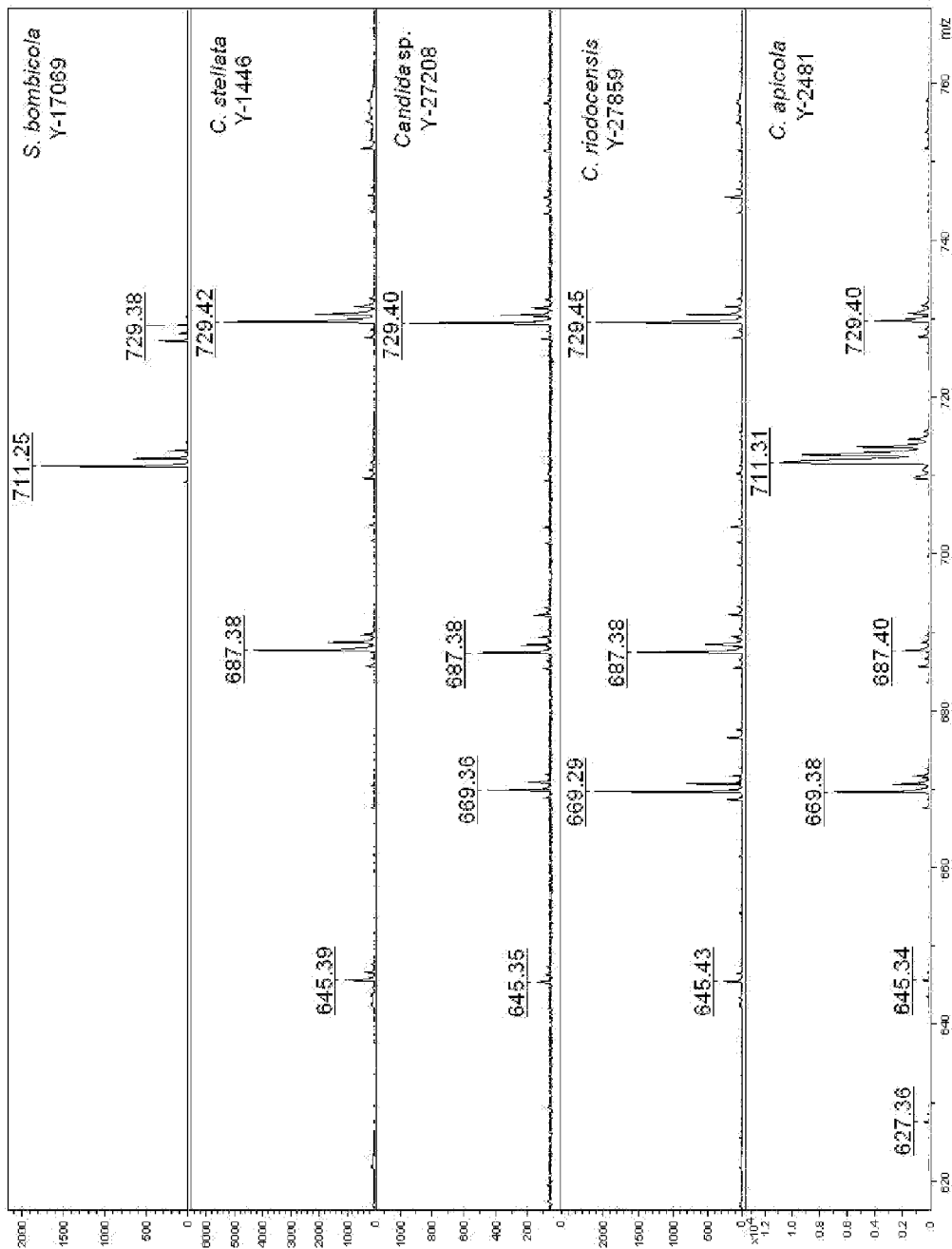
FIG. 2 shows the pile-up of MALDI mass spectra of the sophorolipids from the five major producing *Candida* species as described in Example 1.

The solvent extracts obtained from all 26 strains examined were initially screened for the presence of sophorolipids by MALDI-MS using techniques developed previously by Price et al. (2009. ibid). The spectra were characterized by molecular adduct ions for sophorolipids in the mass range 620-720 Da (FIG. 2). Major ions at m/z 711 and m/z 729 are respectively attributed to the [M+Na]$^+$ molecular adduct ions for the lactone and free acid forms of the major di-acetylated sophorolipid, 6',6''-O-diacetyl-β-D-glucopyranosyl-2$^1$-O-β-D-glucopyranosyl-oxy-octadecenoic acid (Asmer et al. 1988. J Am. Oil Chem. Soc. 65:1460-1466). The observed 18 Da difference between these two ions corresponds to the mass difference between the free carboxylic acid form and the ester-linked 4'-O-lactone (FIG. 2). Less intense ions at m/z 669 and m/z 687 correspond to the mono-acetylated forms of the major sophorolipids, and m/z 627 and m/z 645 to the non-acetylated forms (FIG. 2). The 18 Da mass difference between these two sets of ions is again indicative of the free acid and lactone forms of the minor sophorolipids, and the 42 Da difference between di-, mono-, and non-acetylated species is characteristic of O-linked acetyl groups (Price et al. 2009. ibid). Similar sophorolipid ions were also observed previously for *C. bombicola* by fast atom bombardment mass spectrometry (Asmer et al. 1988. ibid; De Koster et al. 1995. Anal. Biochem. 230:135-148).

The five species of the *Starmerella* clade tested that showed the most prominent production of sophorolipids, *S. bombicola* NRRL Y-17069, *C. stellata* NRRL Y-1446, the new species of *Candida*, NRRL Y-27208, *C. riodocensis* NRRL Y-27859, and *C. apicola* NRRL Y-2481, were further examined by MALDI-MS. These five strains showed a clear structural diversity for the sophorolipids produced (FIG. 2). *S. bombicola* NRRL Y-17069 produced a major di-O-acetylated lactone form of sophorolipid ([M+Na]$^+$, m/z 711), plus a minor component of this as the free acid form ([M+Na]$^+$m/z 729). This latter ion is complicated by an adjacent ion at m/z 727 that is assigned as the potassium adduct ([M+K]$^+$) of the major lactone form. By contrast, *C. stellata*, *Candida* sp. NRRL Y-27208, and *C. riodocensis* produced very little of this lactone form (FIG. 2), and the major ion (m/z 729) for these three species is attributed to a di-O-acetyl free acid form. These strains also produced free acid forms of the mono-acetylated and non-acetylated sophorolipids characterized by MALDI-MS ions at m/z 687 and m/z 645. *C. riodocensis* and *Candida* sp. NRRL Y-27208, but not *C. stellata*, also produced mono-acetylated sophorolipid in the lactone form ([M+Na]$^+$, m/z 669). The greatest heterogeneity for sophorolipid production was observed for *C. apicola* NRRL Y-2481. Like *S. bombicola*, this strain mainly produced lactone sophorolipids, although with *C. apicola*, the di-O-acetyl (m/z 711), mono-O-acetyl (m/z 669) and non-acetyl (m/z 627) forms were observed. The free acid forms of these three sophorolipids were also observed as minor components from *C. apicola*, as characterized by ions 18 Da larger at m/z 729, m/z 687, and m/z 645, respectively (FIG. 2). Interestingly, the free acid form was the major component of sophorolipids produced by *C. batistae* (Konoshi et al. 2008. ibid).

CONCLUSIONS

This study demonstrated that in addition to *S. bombicola*, *C. apicola* and *C. batistae*, three other species of the *Starmerella* clade synthesize significant amounts of sophorolipids, i.e., *Candida riodocensis*, *C. stellata* and *Candida* sp. NRRL Y-27208. Based on our phylogenetic analysis, sophorolipids were produced only by members of the *S. bombicola* subclade of the *Starmerella* clade.

MALDI-MS showed certain of the species to produce sophorolipids predominantly in the lactone form whereas the other species predominantly gave the free acid form. It should be noted that although MALDI mass spectrometry is well suited for the rapid screening and characterization of sophorolipids with diverse molecular mass, it is unable to distinguish between positional isomers, such as differences in the location of acetyl groups, or the fatty acid double bond or acyl-glycosidic linkage. A more complete structural characterization of the sophorolipids from *Candida* sp. NRRL Y-27208 is described in Example 2 below.

TABLE 1

Production of sophorolipids by *Starmerella bombicola* NRRL Y-17069 and *Candida* sp. NRRL Y-27208 over a period of 168 h[1].

| | Sophorolipids produced ($gL^{-1}$)/ Oleic acid consumed ($gL^{-1}$ residual) | |
|---|---|---|
| Time (h) | *S. bombicola* NRRL Y-17069 | *Candida* sp. NRRL Y-27208 |
| 24 | 0.7/83.4 | 0.6/84.5 |
| 48 | 11.8/65.4 | 3.4/79.2 |
| 72 | 54.4/28.7 | 11.0/64.3 |
| 96 | 61.0/33.9 | 11.4/67.8 |
| 120 | 62.6/27.3 | 30.4/35.9 |
| 144 | 64.0/23.5 | 39.6/14.8 |
| 168 | 63.6/16.3 | 44.5/6.2 |

[1]Growth was in SL medium, 25° C., with a shaker speed of 200 rpm. The initial concentration of oleic acid was 87.5 $gL^{-1}$.

TABLE 2

Effect of glucose concentration and shaker speed on production of sophorolipids by *Starmerella bombicola* NRRL Y-17069 and *Candida* sp. NRRL Y-27208.

| | Sophorolipids produced ($gL^{-1}$)/ Oleic acid consumed ($gL^{-1}$ residual) | |
|---|---|---|
| Growth conditions | *S. bombicola* NRRL Y-17069 | *Candida* sp. NRRL Y-27208 |
| Glucose concentration[1] | | |
| 50 $gL^{-1}$ | 48.8/9.7 | 29.0/16.7 |
| 100 $gL^{-1}$ | 69.9/10.3 | 38.6/18.3 |
| 150 $gL^{-1}$ | 95.4/10.0 | 50.1/8.2 |
| Shaker speed[2] | | |
| 150 rpm | 35.6/52.5 | 3.5/78.7 |
| 200 rpm | 62.2/34.2 | 19.8/57.8 |
| 250 rpm | 62.6/31.1 | 24.7/50.2 |
| 300 rpm | 67.9/27.1 | 30.9/45.6 |
| 350 rpm | 75.1/19.4 | 27.1/50.3 |
| 400 rpm | 76.4/18.3 | 27.0/51.4 |

[1]SL medium with glucose concentrations as indicated, shaker speed 200 rpm, incubation 168 h, 25° C.
[2]SL medium with glucose 100 $gL^{-1}$, initial oleic acid concentration 87.5 $gL^{-1}$, incubation 96 h, 25° C.

Example 2

This example describes the structure of the sophorolipids produced by *Candida* sp. NRRL Y-27208.
Materials

*Candida* species were obtained from the ARS Culture Collection (NRRL) at NCAUR, Peoria, Ill. Oleic acid (technical grade at 90% purity) was from Aldrich. All other chemicals were reagent grade and used without further purification.
Yeast Fermentation and Extraction

*Candida* species were grown in 3 mL of YM medium which contained 5 g/L peptone, 10 g/L glucose, 3 g/L yeast extract, and 3 g/L malt extract in a test tube at 25° C., 200 rpm for 24 hours. This culture was used to inoculate (1%) the production medium (10 mL), 100 g/L glucose, 100 mL/L oleic acid, 1.5 g/L yeast extract, 4 g/L $NH_4Cl$, 1 g/L $KH_2PO_4$, 0.1 g/L NaCl, 0.5 g/L $MgSO_4$ in a 50 mL Erlenmeyer flask. This was cultivated at 25° C., 200 rpm, for typically 96 hours. The pH was adjusted to ~3.5 at 24, 32, 48, and 56 hours into the reaction using 1M NaOH. The samples that included both cells and broth were acidified to pH 2 and extracted twice with 40 mL ethyl acetate. Solvents were evaporated from the combined extracts with a rotary evaporator. The oleic acid was separated from the remaining sophorolipids with hexane washes with the oleic acid in the hexane. The purified sophorolipids were analyzed using MALDI-TOFMS. Compositional analysis by gas chromatography/mass spectrometry (GC-MS)

Samples were hydrolyzed in trifluoroacetic acid (2 M, 110° C., 30 min) on a reaction block. After cooling, the solvent was removed by evaporation and aldononitrile acetates were prepared as described previously.[19] GC-MS analysis was performed on an Agilent (Santa Clara, Calif.) 6890N gas chromatograph interfaced with an Agilent 5973N mass-selective detector configured in electron impact (EI) mode, and with a Hewlett Packard (Santa Clara, Calif.) 7683 series autoinjector. Chromatography was achieved on a Hewlett Packard DB-5 ms column (30 m by 0.2 mm) using helium as the carrier. The oven temperature was ramped over a linear gradient from 150 to 300° C. at 10° C. per min. Mass spectra were recorded in positive-ion mode over the range m/z 60 to 550. Injector and detector/interface temperatures were 275 and 300° C., respectively. Data analysis was done off-line using HP Chemstation.
Surface Tension Measurements The surface tension of sophorolipid solutions was determined using the pendant drop method. Samples were prepared with deionized distilled water and analyzed with FTA 4000 surface tension instrument (First Ten Angstroms inc. Portsmouth, VA). Measurements were made with a 22 gauge blunt needle with a 6 µl drop. The values reported represent an equilibrium surface tension determined 150 seconds after drop formation. The reported values are the average of a minimum of 3 separate measurements. The critical micelle concentration determined with software provided by the instrument's manufacturer (FTA32 version 2.0 build 275).
MALDI-TOFMS Analysis MALDI-TOF mass spectra were recorded on a Bruker Daltonic Omniflex instrument (Bruker Daltonics, Billerica, Mass.) operating in reflectron mode. Samples were typically dissolved in acetonitrile, and the matrix used was 2,5-dihydrobenzoic acid. The samples plus matrix were dried onto the 49-place target at room temperature prior to introduction into the spectrometer. Ion source 1 was set to 19.0 kV, and source 2 to 14.0 kV, with lens and reflector voltages of 9.20 and 20.00 kV, respectively. A 200 ns pulsed ion extraction was used with matrix suppression up to 200 Da. The instrument was calibrated externally on a dp series of malto-oligosaccharides. Excitation was at 337.1 nm, typically at 60% of 150 µJ maximum output, and 80 shots were accumulated. The reflectron mass resolution (FWHM) for m/z=2465 (ACTH 18-39) was >20,000.
Nuclear Magnetic Resonance (NMR) Spectroscopy All NMR experiments were performed on a Bruker Avance spectrometer (Bruker BioSpin Corp., Billerica, Mass.) operating at 500.11 Mhz using a standard 5 mm z-gradient BBI probe at 27° C. Chemical shifts are reported as ppm from tetramethylsilane calculated from the lock solvent. The deuterated solvents used were obtained from Cambridge Isotope Labs (Andover, Mass.). The pulse sequences used were those supplied by Bruker, and processing was done with the Bruker TOPSPIN software package (version 1.3).
Results and Discussion
MALDI-TOFMS Analysis The sophorolipids were isolated from *S. bombicola* NRRL Y-17069 and *Candida* sp. NRRL Y-27208 grown in liquid culture on glucose plus oleic acid, as described previously.[17] The MALDI-TOFMS-based screen identified m/z 711 as the major [M+Na]$^+$ ion arising from the *S. bombicola* sophorolipids, whereas those from *Candida* sp. NRRL Y-27208 gave ions at m/z 729, 687, 669, and 645.[17] Noticeably, the *S. bombicola* major sophorolipid was absent from the NRRL Y-27208 extract, although the 18 Da mass difference between m/z 711 and m/z 729 indicated that these ions are due to lactone and free carboxylic acid form sophorolipids, respectively. Hence, these major sophorolipid species were assigned as the lactone and free acid forms of a di-O-acetyl sophorolipid, 6',6"-O-diacetyl-β-D-glucopyranosyl-2$^1$-O-β-D-glucopyranosyl-oxy-octadecenoic acid. Smaller ions from the NRRL Y-27208 sophorolipids, at m/z 687 and 645 were attributed to mono-O-acetyl and non-O-acetyl analogs of this major free acid sophorolipid, with a minor ion at m/z 669 indicating the mono-O-acetyl sophorolipid in a lactone form.[17]

Figure 3:
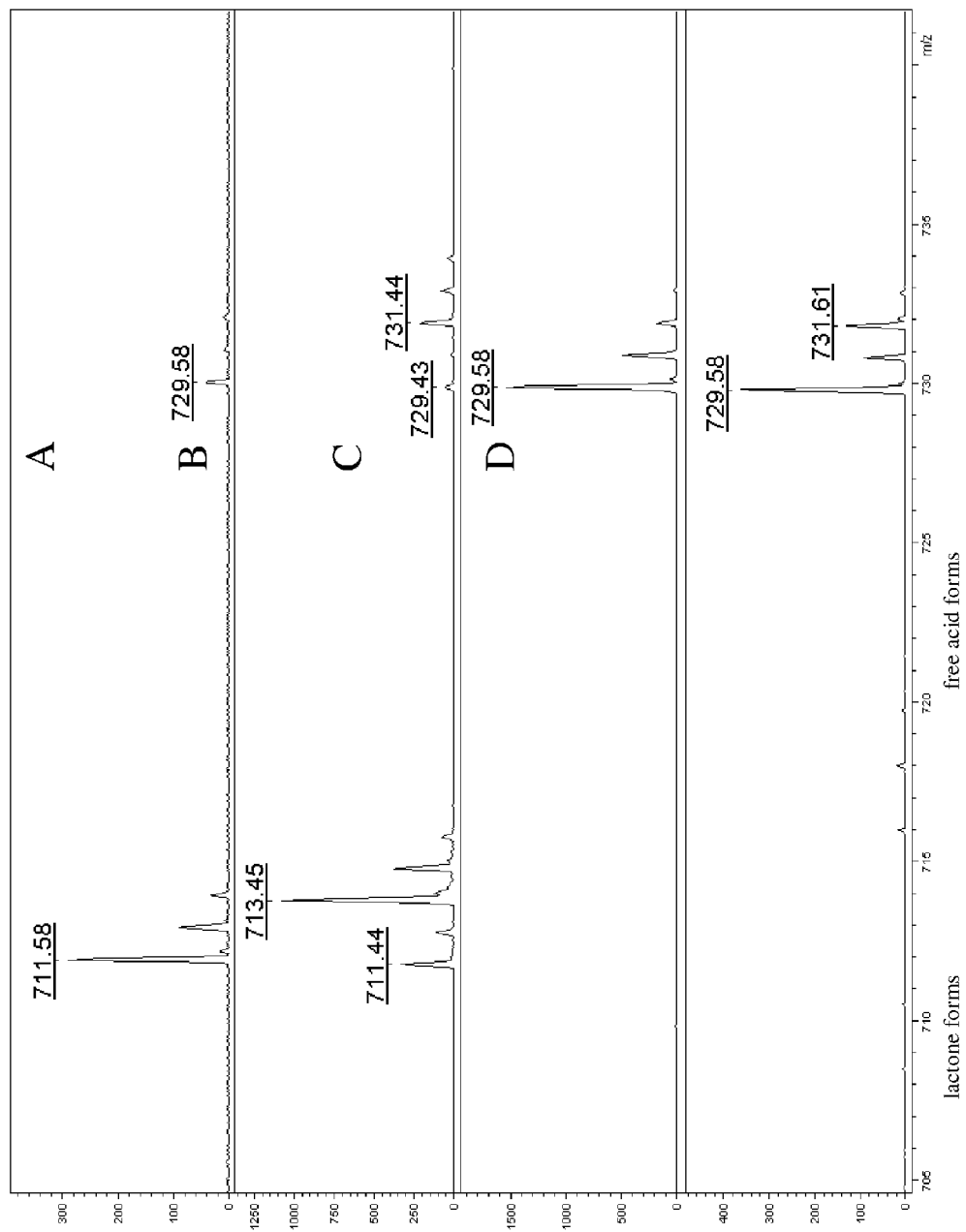
FIG. 3 shows the MALDI-TOFMS analysis of sophorolipids from *Candida* yeast strains grown on different fatty acids as described in Example 2. *S. bombicola* grown on oleic (A.) and stearic acid (B.). *Candida* sp. NRRL Y-27208 grown on oleic (C.) and stearic acid (D.). The observed ions correspond to 6',6"-O-diacetyl-β-D-Glcp-21-O-β-D-Glcp-oxy-oleate-type sophorolipids in lactone (m/z 711) or free acid (m/z 729) forms, plus 6',6"-O-diacetyl-β-D-Glcp-21-O-β-D-Glcp-oxy-stearate-type sophorolipids in the corresponding lactone (m/z 713) or free acid (m/z 731) forms.

Growth of these *Candida* yeasts on different fatty acid substrates resulted in the formation of various sophorolipid structures, as determined by MALDI-TOFMS (FIG. 3). Hence, *S. bombicola* grown on oleic acid produced a 6',6"-O-diacetyl-β-D-Glcp-2$^1$-O-β-D-Glcp-oxy-oleate (oxy-octadecenoate) lactone-type sophorolipid that is characterized by m/z 711 ions, plus a smaller ion (m/z 729) due to the free acid form (FIG. 1. A). These ions were also seen when *S. bombicola* was cultured on stearic acid, but in this case more major ions were observed that are two mass units larger, at m/z 713 and 731 (FIG. 3. B). These are attributed to the formation of 6',6"-O-diacetyl-β-D-Glcp-2$^1$-O-β-D-Glcp-oxy-stearate (oxy-octadecanoate)-type sophorolipids, plus smaller amounts of the previously observed 6',6"-O-diacetyl-β-D-Glcp-2$^1$-O-β-D-Glcp-oxy-oleate (oxy-octadecenoate)-type. In contrast, *Candida* sp. NRRL Y-27208 grown on oleic acid produced only 6',6"-O-diacetyl-β-D-Glcp-2$^1$-O-β-D-Glcp-oxy-oleate-type sophorolipid in the free acid form, with no evidence of lactone formation (FIG. 3. C). This was also the major sophorolipid produced when this strain was grown on stearate, plus a minor amount of 6',6"-O-diacetyl-β-D-Glcp-2$^1$-O-β-D-Glcp-oxy-stearate, which is also in the free acid form (m/z 731, FIG. 3. D)

Lipid and Sugar Compositional Analysis by GC-MS

Figure 4:
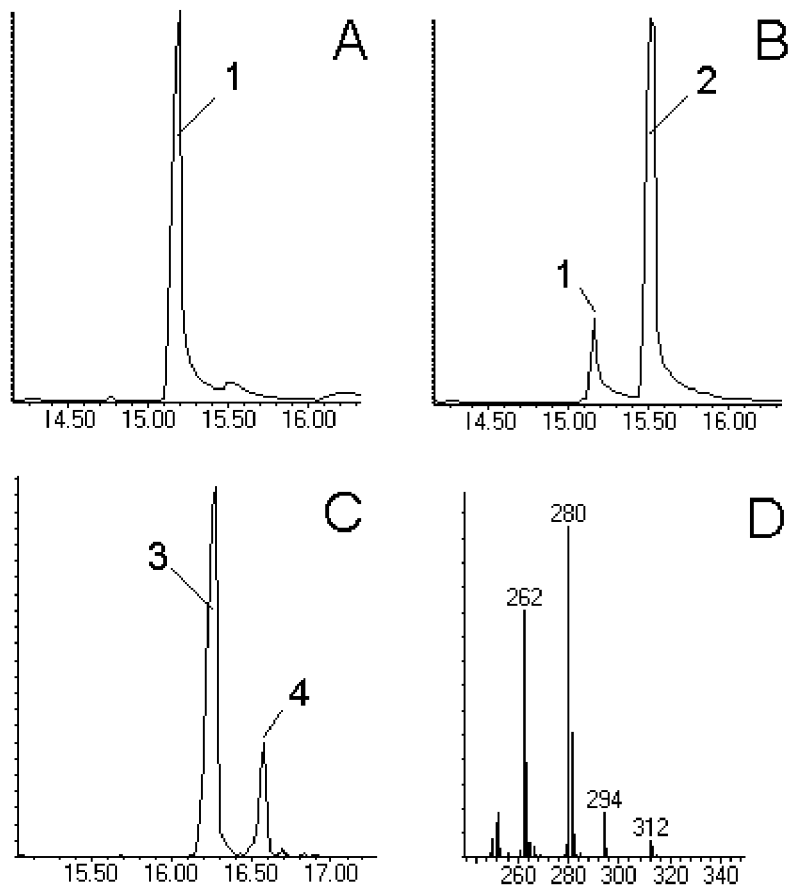
FIG. 4 shows the GC-MS analysis of hydroxyl fatty acids from *Candida* sophorolipids grown on different substrates as described in Example 2. A. *S. bombicola* grown on oleate; B. *S. bombicola* grown on stearate; C. *Candida* sp. grown on oleate. The acid hydrolyzed fatty acids were analyzed as the methyl esters. 1. 17-hydroxyoleate, $t_R$=15.2 min.; 2. 17-hydroxystearate, $t_R$=15.5 min.; 3. 18-hydroxyoleate, $t_R$=16.3 min.; 4. 20-hydroxy-C20:1, $t_R$=16.6 min. Panel D shows a detail of the EIMS spectrum of GC peak 3, and is discuss in the main text. $t_R$=retention time.

To confirm the MALDI-TOFMS assignments and provide additional structural data the sophorolipid extracts were hydrolyzed and analyzed by GC-MS for composition analysis. Analysis of fatty acid methyl esters by GC-MS revealed that the *S. bombicola* and *Candida* sp. strains produce sophorolipids that contain different acyl groups. When *S. bombicola* was grown on oleic acid (octadecenoate) the major sophorolipid fatty acid observed is 17-hydroxyoleic fatty acid (17-hydroxyoleate, $t_R$ 15.1 min. FIG. 4, panel A). The methyl 17-hydroxyoleate gave a GC-EIMS molecular ion at m/z 312 and (M-18) at m/z 294, plus fragment ions characteristic of (ω-1) hydroxyl fatty acids.[20] This is also consistent with the oleate-type sophorolipids ions m/z 711 and 729 observed by MALDI-TOFMS; FIG. 3, panel A). When grown on stearic acid (octadecanoic acid) *S. bombicola* produced sophorolipids that contain predominantly 17-hydroxy-octadecanoate (17-hydroxystearic, Rf=15.5 min. FIG. 4. panel B). The 17-hydroxystearic methyl ester gave no observable molecular ion, but was identified by a strong (M-44) fragment ion (m/z 270) arising from characteristic cleavage alpha to the 17-hydroxy group.[20] A smaller GC peak (Rf=15.1 min) was attributed to 17-hydroxy-octadecenoic (17-hydroxyoleic acid), and arises from the 6',6"-O-diacetyl-β-D-Glcp-2$^1$-O-β-D-Glcp-oxy-oleate-type sophorolipids, as also observed by MALDI-TOFMS as m/z 711 or m/z 729 ions (FIG. 4, panel B).

Sophorolipids from the newly identified *Candida* sp. NRRL Y-27208 did not contain 17-hydroxy fatty acid, but rather a new GC-MS peak was observed at $t_R$ 16.2 min, plus a smaller peak at 16.5 min (FIG. 4, panel C). The larger peak (peak 3) was characterized as 18-hydroxyoleate by EIMS ions at m/z 312 (M$^+$) and m/z 294 (M-18). In addition, (M-CH$_2$OH) was observed at m/z 280 and (M-CH$_2$OH—H$_2$O) at m/z 262 (FIG. 4. Panel D). The smaller GC peak (peak 4) gave rise to M$^+$ at m/z 340, (M-18) at m/z 322, (M-CH$_2$OH) at m/z 308, and (M-CH$_2$OH—H$_2$O) at m/z 290 (data not shown), suggesting that a minor amount of 20-hydroxy-C$_{20:1}$ fatty acid is also present. Taken together with the MALDI-TOFMS and NMR data the fatty acid analysis support the conclusion that *S. bombicola* produces sophorolipids that contain 17-hydroxyoleic or 17-hydroxystearic acyl groups, the majority of which are in a 1,4'-lactone formation, whereas *Candida* sp. NRRL Y-27208 sophorolipids contain an ω-hydroxyacyl group, predominantly 18-hydroxyoleic, in the open chain, free acid form.

Acid hydrolyzed or saponified samples were also derivatized to form volatile aldononitrile peracetates (PAANs) suitable for GC-MS analysis of monosaccharides. For the sugar derivatives, a single GC peak was observed that co-eluted with a standard of D-glucose PAAN. The MS spectrum arising from this peak showed fragment ions that are characteristic of hexoses and was identical to the standard D-glucose PAAN.[19] The sugar composition of the sophorolipid head-groups was consistent whether the producing yeast strains were cultured on glucose, xylose, mannose, or galactose as the carbohydrate source (data not shown). Hence, sophorolipids with alternative sugar head groups were not observed.

Sophorolipid Surfactant Properties

Figure 5:
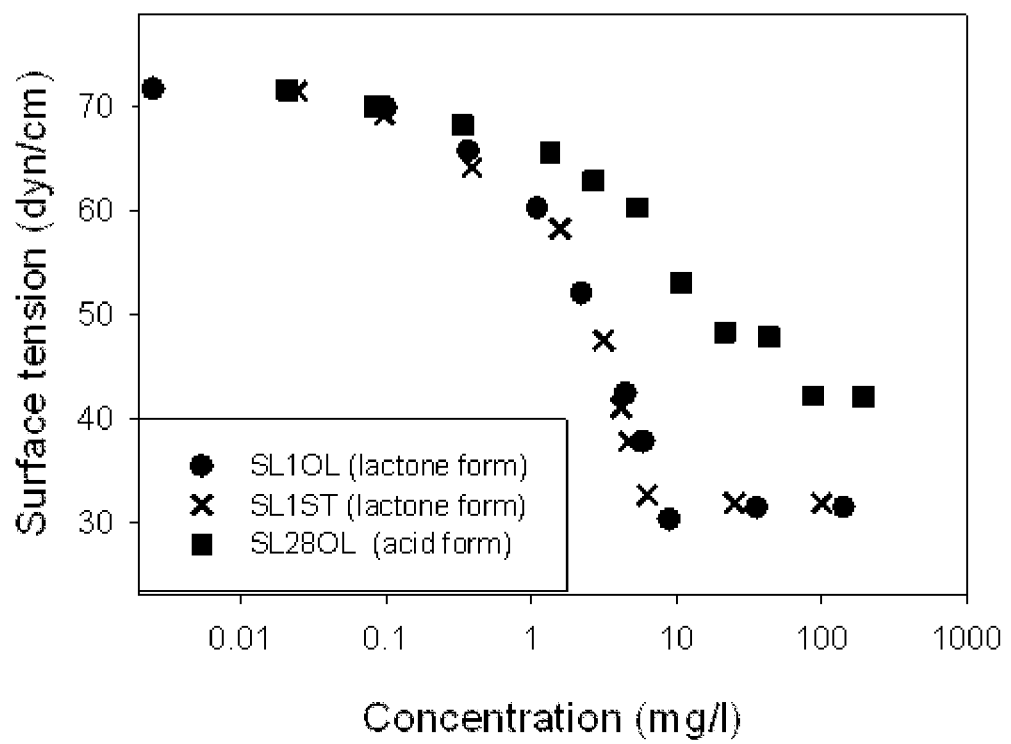
FIG. 5 shows the surface tension properties as determined using the pendant drop method as described in Example 2. The equilibrium surface tension was measured 150 seconds after drop formation. The critical micelle concentrations (CMCs) calculated for the sophorolipids are *S. bombicola* 17-hydroxyoleate-type sophorolipid in 1,4'-lactone form (SL1OL)=6.9 mg·L$^{-1}$; *S. bombicola* 17-hydroxystearate-type sophorolipid in 1,4'-lactone form (SL1ST)=5.6 mg·L$^{-1}$; and new *Candida* sp.-type 18-hydroxyoleate-type sophorolipid in open chain, anionic form (SL28OL)=46.4 mg·L$^{-1}$.

Surface tension properties of the sophorolipids were determined using the pendant drop method (FIG. 3). The critical micelle concentrations (CMCs) for the sophorolipids differed by stain, and hence by the nature of the acyl chain and whether it is in the open or lactone form. *S. bombicola* sophorolipids 6',6"-O-diacetyl-β-D-Glcp-2$^1$-O-β-D-Glcp-17-hydroxystearate 1,4'-lactone and 6',6"-O-diacetyl-β-D-Glcp-2$^1$-O-β-D-Glcp-17-hydroxyoleate 1,4'-lactone have measured CMCs of 5.6 mg/L and 6.9 mg/L, respectively. The novel anionic, open chain sophorolipid 6',6"-O-diacetyl-β-D-Glcp-2$^1$-O-β-D-Glcp-18-hydroxyoleic from *Candida* sp. NRRL Y-27208 has a CMC of 46.4 mg/L (FIG. 5). These properties are consistent with those found previously for sophorolipids that had been chemically modified to open the lactone ring.[21]

Naturally Occurring Dimeric and Trimeric Sophorolipids

Figure 6:
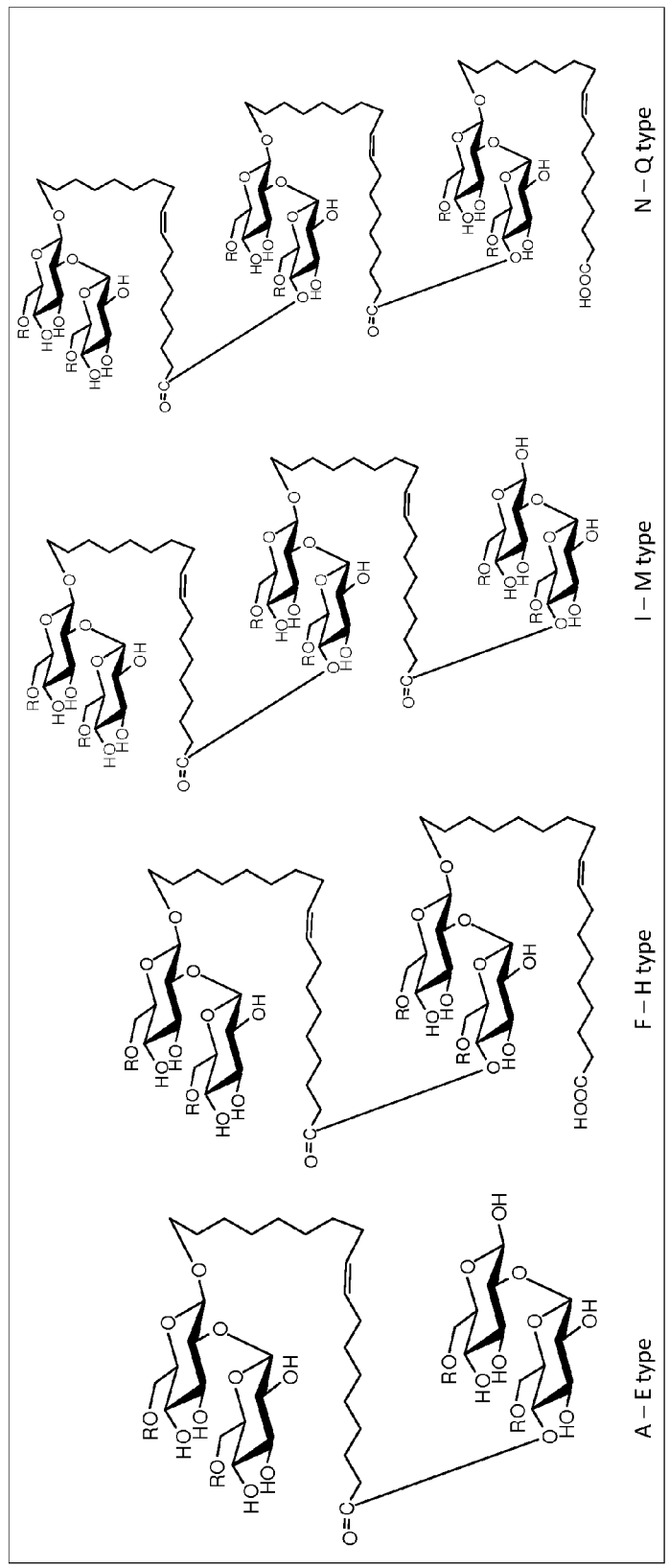
FIG. 6 shows the structure of dimeric and trimeric sophorolipids as described in Example 2. Seventeen polymeric sophorolipids (A-Q) were detected by MALDI-TOFMS, as shown in FIGS. 7 and 8 A-E, mono-acyl-disophorose; F-H, di-acyl-disophorose; I-M, di-acyl-trisophorose; N-Q, tri-acyl-trisophorose. —OR=O-acetyl groups. The calculated [M+Na]+ masses (in Daltons) are A, 969.47; B, 1011.48; C, 1053.48; D, 1095.49; E, 1137.50; F, 1333.73; G, 1375.73; H, 1417.74; I, 1657.85; J, 1699.86; K, 1741.86; L, 1783.86; M, 1825.87; N, 1980.10; O, 2022.10; P, 2064.11; Q, 2106.11.
Figure 7:
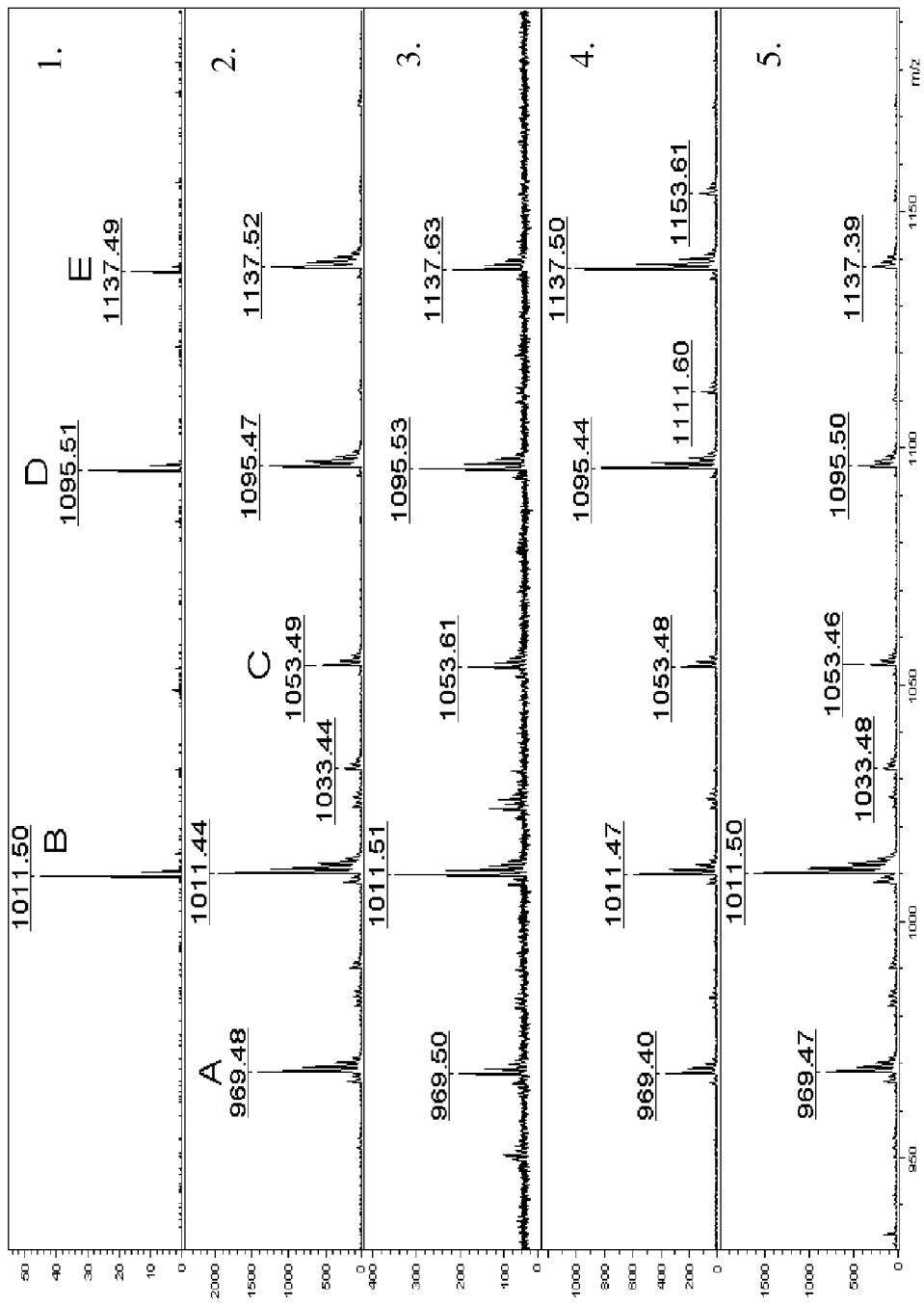
FIG. 7 shows the MALDI TOF/MS spectra of dimeric sophorolipids produced as described in Example 2 by five species of the *Starmerella* yeast clade: 1. *S. bombicola* NRRL Y-17069, 2. *C. stellata* NRRL Y-1446, 3. *Candida* sp. NRRL Y-27208, 4. *C. riodocensis* NRRL Y-27859, and 5. *C. apicola* NRRL Y-2481. The observed {M+Na}+ ions (A-E) are due to sophorolipid dimers in which two sophorose units are linked via a hydroxyoleate group. The mass difference of 42 Da indicates non-O-acetyl (A), mono-O-acetyl (B), di-O-acetyl (C), tri-O-acetyl (D), and tetra-O-acetyl (E) structures. The structures are shown in FIG. 6.
Figure 8:
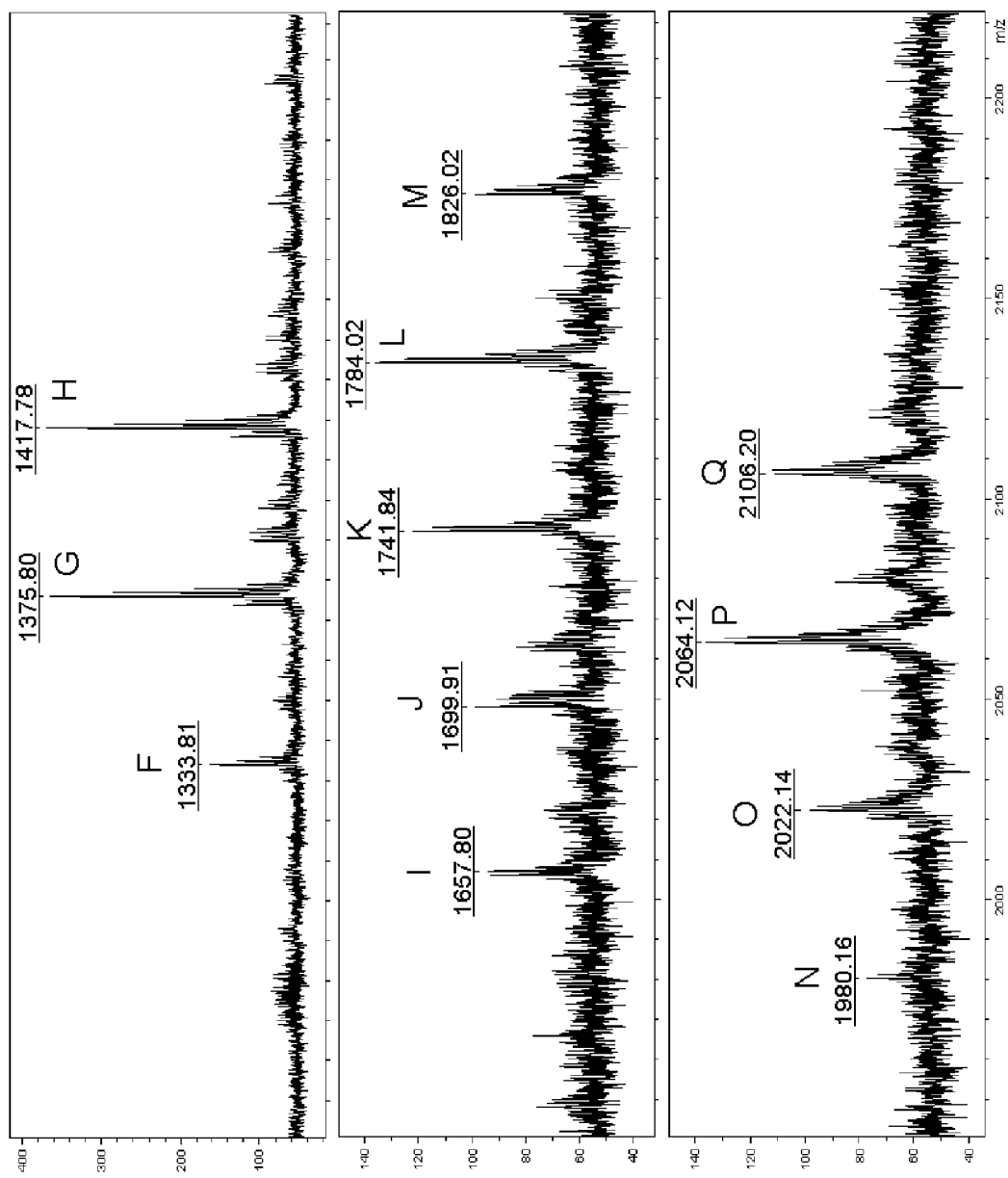
FIG. 8 shows the MALDI TOF/MS spectra of polymeric sophorolipids from *Candida* sp. NRRL Y-27208 as described in Example 2. Sophorolipid dimers with two hydroxyoleic acyl chains (F-H), with 42 Da mass difference due to di-O-acetyl (dimer F), tri-O-acetyl (dimer G), and tetra-O-acetyl (dimer H) species. In addition, sophorolipid trimers (I-J) with three sophorose units linked by two hydroxyoleic groups, and are either di- (I), tri- (J), tetra- (K), penta- (L), or hexa-O-acetyl (M). The larger ions (N-Q) correspond to trimeric sophorolipids linked by three acyl chains, thus, tri- (N), tetra- (O), penta- (P), and hexa-O-acetyl (Q) species. The structures are shown in FIG. 6. These twelve polymeric sophorolipids (F-Q) were only detected as produced by the new *Candida* sp. NRRL Y-27208.

Examination of the higher mass range in the MALDI-TOFMS spectra led to the identification of several previously undescribed polymeric sophorolipids (FIGS. 7, 7 and 8). In the mass range 950-1200 Da five dimeric sophorolipids (A-E) were detected. These were present in varying amounts in the five *Starmerella* yeast strains tested (FIG. 7). Sodium adduct [M+Na]$^+$ ions observed at m/z 969.47 (A), 1011.48 (B), 1053.48 (C), 1095.49 (D), and 1137.50 (E) are attributable to dimeric sophorolipids, in which the free carboxylic acid of one sophorose monomer is ester linked to a second monomer (see structures in FIG. 6). The 42 Da mass differences between these ions indicated that they are dues to non-O-acetyl, mono-O-acetyl, di-O-acetyl, tri-O-acetyl, and tetra-O-acetyl dimers. *S. bombicola* produced conspicuously less of these dimeric sophorolipids, relative to the other four strains analyzed, and only dimers B, D, and E were detected (FIG. 7). The new *Candida* species, NRRL Y-27208, produced greater quantities, predominantly mono-O-acetyl dimer B and tri-O-acetyl dimer D, as well as several larger polymeric compounds (described below). The MALDI-TOFMS dimer profile for *C. stellata* and *C. apicola* were similar to that of *Candida* sp. NRRL Y-27208, but these strains did not produce the larger sophorolipid polymers. C. riodocencis also produced five dimers, although in this case the major compounds detected were the tetra-O-acetyl dimer E and the tri-O-acetyl dimer D (FIG. 7).

Additional MALDI-TOFMS ions were detected for dimeric sophorolipid (assigned as F-H) in the mass range m/z 1300-1450 (FIG. 8, panel 1). These masses correlate with sophorolipid dimers with two acyl chains, and the 42 Da mass difference between them indicating di-O-acetyl (dimer F), tri-O-acetyl (dimer G), and tetra-O-acetyl (dimer H) species. Unlike the smaller, monoacylated dimers, these diacylated dimeric sophorolipids were only produced by the new species *Candida* sp. NRRL Y-27208, and comparable polymeric compounds were not seen from the *S. bombicola* strain or with the other yeast species included in our initial screening.[17] In addition, the new strain *Candida* sp. NRRL Y-27208 produced nine trimeric sophorolipids, five (I-M) in the mass range 1600-1850 Da, and four (N-Q) in the range 1950-2150 Da (FIG. 8, panels 2 and 3). Sophorolipid trimers I-J correspond to the masses of three sophorose units linked by two acyl groups, and are either di-(I), tri- (J), tetra- (K), penta- (L), or hexa-O-acetyl (M). The larger ions, m/z 1980.16, 2022.14, 2064.12, 2106.20 (FIG. 8, panel 3) correspond to trimeric sophorolipids linked by three acyl chains, and were designated as the tri- (N), tetra- (O), penta- (P), and hexa-O-acetyl (Q) species. As with the diacylated dimers (sophorolipids F-H), all of these trimeric sophorolipids were only detected as produced by the new *Candida* sp. NRRL Y-27208.

1D and 2D NMR Assignments

Figure 9:
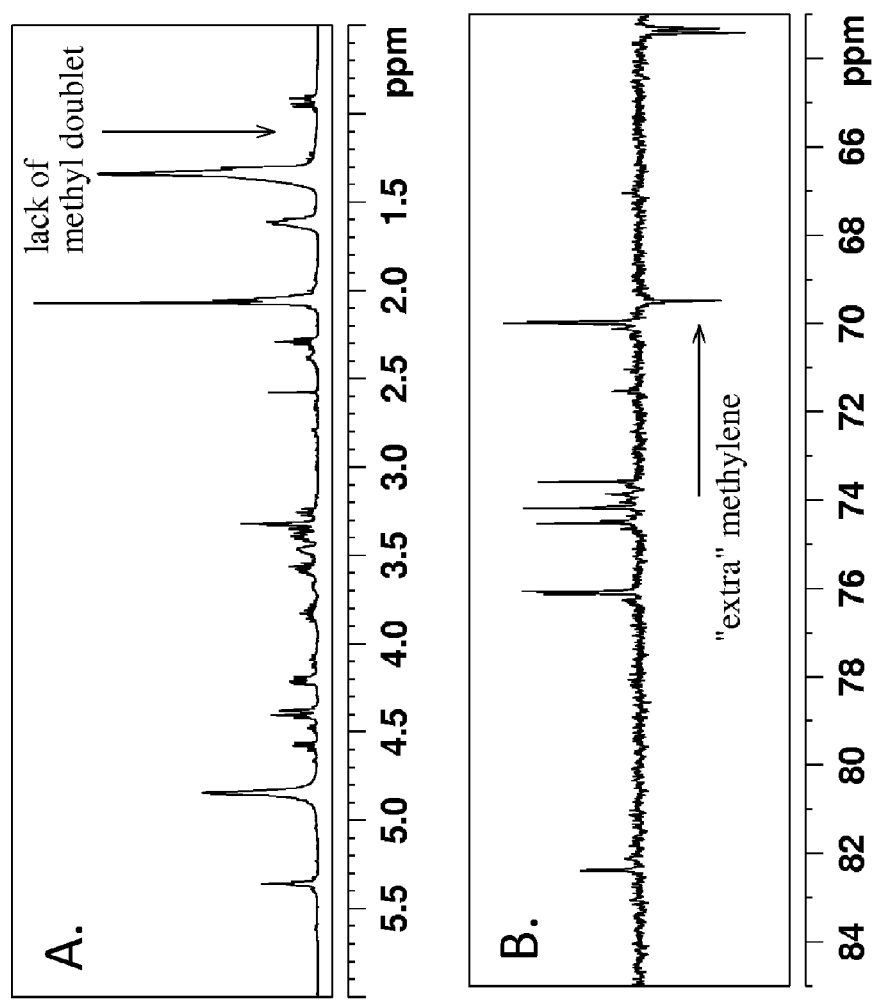
FIG. 9 shows the NMR data obtained on sophorolipids from new species *Candida* sp. NRRL Y-27208 as described in Example 2. The data support the non-lactone, anionic form of the sophorolipids, and the presence of the unusual ω-hydroxy-linked 18-hydroxyoleic group.

The NMR spectra of the sophorolipids are dominated by essentially three spin systems: 1. the 2-O-linked β-D-glucosyl residue (numbered C-1" to C-6"); 2. the acylhydroxy-linked β-D-glucosyl residue (numbered C-1' to C-6'); and, 3. the hydroxylacyl group (numbered C-1 to C-18). The numbering system follows that of de Koster et al.[22] NMR assignments have been reported previously for sophorolipids from *Candida bombicola*(De Koster et al. 1995. Ibid), *Candida* (*Torulopsis*) *apicola* (Weber et al. 1990. Carbohydr. Res. 206:13-19), *Candida* (*Torulopsis*) *bombicola* ATCC 22214 (Asmer et al. 1988. Ibid) and for lipase-modified sophorolipids from *Candida* (*Torulopsis*) *bombicola* (Bisht et al. 1999. J. Org. Chem. 64:780-789), and our current findings confirm these general structural assignments. Hence, NMR signals due to the glucosyl anomeric nuclei are evident for the *S. bombicola* sophorolipid H-1'/C-1' at 4.46 ppm/102.2 ppm and H-1"/C-1" at 4.63 ppm/104.0 ppm, and for the *Candida* sp. NRRL Y-27208 sophorolipid H-1'/C-1' at 4.46 ppm/101.1 ppm and H-1"/C-1" at 4.57 ppm/104.2 ppm (Table 3). The fatty acid 9, 10-double bond is also evident for both sophorolipids at 5.35 ppm/129.3 ppm and 5.36 ppm/129.5 ppm (Table 3). In this example we will therefore focus on the structural difference between the sophorolipids from *S. bombicola* NRRL Y-17069 and those of the new strain *Candida* sp. NRRL Y-27208 (FIG. 9).

For the *S. bombicola* sophorolipids the anomeric H-1" signal at 4.63 ppm shows a HMBC long range coupling across the 1"-anomeric oxygen to the C-2' carbon (C-2', 82.3 ppm) on the other glucosyl ring. This, and the chemical shift differences between the H-2'/C-2' nuclei (3.42 ppm/82.3 ppm) and the H-2"/C-2" nuclei (3.33 ppm/75.3 ppm) are supportive evidence for the β-1,2-O-glycoside linkage between the glucosyl rings. The other glucosyl anomeric signal, H-1', also shows a HMBC long rang coupling, in this case to the methine C-17 acyl carbon at 78.7 ppm. An HSQC experiment revealed that this C-17 carbon is coupled to the adjacent H-17 proton at 3.76 ppm. This proton signal is noticeably shifted by the attached 17-hydroxy group which is O-glycosidically linked to the Glc-1' ring. Hence, it is observed as an "extra" CHOH methine signal in the HSQC and DEPT spectra. Noticeably, the corresponding H-17/C-17 for the new *Candida* sp. sophorolipid gave rise to NMR signals at 1.61 ppm/29.3 ppm, which are characteristic of a non-hydroxylated methylene group.

The terminal acyl methyl group of the *S. bombicola* sophorolipids is assigned by H-18/C-18 NMR signals at 1.22 ppm/20.2 ppm (Table 3). The H-18 proton showed a small hertz coupling to the previously assigned C-17 "extra" CHOH, resulting in a doublet at 1.22 ppm. This coupling was also evident in the TOCSY and COSY correlation spectra (data not shown). Noticeably, as discussed below, this evidence for a terminal methyl doublet was absent for the *Candida* sp. NRRL Y-27208 sophorolipids.

A DEPT spectrum of the *S. bombicola* sophorolipids revealed two methylene carbons at 62.4 ppm and 63.4 ppm which are assigned, respectively, as the glucosyl C-6' and C-6" signals. The HSQC showed that one of these (C-6') was associated with non-equivalent proton signals at 4.11-4.15 ppm and 3.68-3.85 ppm, while the other (C-6") was coupled to overlapping proton signals. These have previously been assigned as due to the lactone and non-lactone (anionic) forms for the *S. bombicola* sophorolipids.[22] This was also evident from the H-4" signals at 4.92 ppm (lactone form) and 3.32 ppm (anionic form) (Table 3). The lactone H-4" signal at 4.92 ppm was evident as a triplet, and also showed a long range coupling to carbon C-5" at 72.0 ppm. The corresponding non-lactone C-5" signal was observed at 76.5 ppm (Table 3).

An equivalent DEPT spectrum for the *Candida* sp. NRRL Y-27208 sophorolipid also revealed two methylene carbons in the 63-64 ppm region (FIG. 9, panels B), which are assigned as C-6' and C-6" (Table 3). These are coupled to overlapping proton signals at 4.21 ppm and at 4.49 ppm. However, for the NRRL Y-27208 sophorolipid an addition methylene group is also evident in the DEPT spectrum at 69.5 ppm (FIG. 9, panel B). This acyl C-18 carbon is coupled to non-equivalent H-18 protons at 3.58 ppm and 3.82 ppm, both of which also show long range HMBC couplings to the anomeric C-1' (101.6 ppm) for this molecule.

Taken together with the MALDI-TOFMS evidence and the GC-MS lipid analysis these NMR data support the conclusion that the major sophorolipids from the new species *Candida* sp. NRRL Y-27208 are comprised of a sophorose unit β-O-glycosidically linked to the 18-hydroxy group of 18-hydroxy-oleic acid. By contrast, the sophorose headgroup of the *S. bombicola* sophorolipids is linked to the ω-1 hydroxyl group of 17-hydroxyoleic acid, similar to that reported by others (Asmer et al. 1988. ibid; De Koster et al. 1995. ibid; Weber et al. 1990. ibid; Bisht et al. 1999. ibid; and Singh et al. 2003. J. Org. Chem. 68:5466-5477). Moreover, when grown on stearic acid *S. bombicola* produces 17-hydroxystearate-containing sophorolipids. In addition, whereas the *S. bombicola* sophorolipid is predominantly in the 1'-4"-lactone form, with lesser amounts of the carboxylate in the free anionic form, the new species *Candida* sp. sophorolipid is entirely in the open free carboxylate form.

The ω-linked sophorolipids described are similar to those recently identified from *Candida batistae* (Konishi et al. 2008. ibid) although phylogenetic analysis shows that the new strain *Candida* sp. NRRL Y-27208 is clearly a different species to *C. batistae* (Kurtzman et al. 2010. ibid). Konishi et al. shows that *C. batistae* produces mixtures of lactone and free acid form sophorolipids, in 40:60 ratio (Konishi et al. 2008. ibid). These are comprised of mixtures of both $C_{18}$-17-OH (i.e. (ω-1)-linked, ~15% of total) and $C_{18}$-18-OH (ω-linked, ~64%) type sophorolipids, plus about 16% unknown (Konishi et al. 2008. ibid). By comparison, our MALDI-TOFMS analyses show that the sophorolipids from *Candida* sp. Y 27208 are all in the open chain free acid form, with no evidence for lactone forms. In addition, *Candida* Y-27208 sophorolipids are all ω-linked, mostly $C_{18}$-18-OH-type but also ~5% of $C_{20}$-20-OH-type, with no evidence for (ω-1)-linked forms. Lastly, *Candida* sp. Y-27208 produces minor amounts of dimeric and trimeric sophorolipids, but these were not detected for *C. batistae* (Konishi et al. 2008. ibid).

TABLE 3

$^1$H and $^{13}$C NMR data and assignments.

| Residue | $^1$H Chemical Shifts | | | $^{13}$C Chemical Shifts | | |
|---|---|---|---|---|---|---|
| | A.[1] | B. | C. | A. | B. | C. |
| D-Glc$^I$ | | | | | | |
| 1' | 4.46 | 4.46 | 4.41 | 102.2 | 101.1 | 101.6 |
| 2' | 3.42 | 3.39 | 3.40 | 82.3 | 82.4 | 82.4 |
| 3' | 3.56 | 3.57 | 3.56 | 76.2 | 76.5 | 76.1 |
| 4' | 3.30 | 3.32 | 3.32 | 70.2 | 70.0 | 70.0 |
| 5' | 3.47 | 3.47 | 3.46 | 73.4 | 73.5 | 74.2 |
| 6' | 4.37, 4.20 | 4.38, 4.20 | 4.39, 4.21 | 62.4 | 63.5 | 63.4 |
| 7' | — | — | — | 171.25 | 171.3 | 171.2 |
| 8' | 2.07 | 2.06 | 2.07 | 19.4 | 19.6 | 19.3 |
| D-Glc$^{II}$ | | | | | | |
| 1" | 4.63 | 4.57 | 4.57 | 104.0 | 104.2 | 104.0 |
| 2" | 3.33 | 3.26 | 3.26 | 75.3 | 74.6 | 74.5 |
| 3" | 3.60 | 3.40 | 3.39 | 73.5 | 76.1 | 76.1 |
| 4" | 4.92 | 3.32 | 3.32 | 70.3 | 70.0 | 70.0 |
| 5" | 3.66 | 3.28 | 3.46 | 72.0 | 76.5 | 73.6 |
| 6" | 4.15, 4.11 | 3.85, 3.68 | 4.39, 4.21 | 63.4 | 61.4 | 63.3 |
| 7" | — | — | — | 170.8 | 171.3 | 171.3 |
| 8" | 2.05 | 2.06 | 2.06 | 19.3 | 19.4 | 19.5 |
| Hydroxyoleic | | | | | | |
| 1 | — | — | — | 173.0 | 176.3 | 176.3 |
| 2 | 2.39 | 2.29 | 2.29 | 33.5 | 33.6 | 33.6 |
| 3 | 1.68 | 1.61 | 1.61 | 24.2 | 24.7 | 24.7 |
| 4-7 | 1.3-1.4 | 1.3-1.4 | 1.3-1.4 | 28-30 | 28-30 | 28-30 |
| 8 | 2.05 | 2.04 | 2.04 | 26.6 | 26.8 | 26.7 |
| 9 | 5.35 | 5.36 | 5.36 | 129.3 | 129.5 | 129.4 |
| 10 | 5.35 | 5.36 | 5.36 | 129.8 | 129.5 | 129.4 |
| 11 | 2.05 | 2.04 | 2.04 | 26.9 | 26.8 | 26.7 |
| 12-14 | 1.3-1.4 | 1.3-1.4 | 1.3-1.4 | 28-30 | 28-30 | 28-30 |
| 15 | 1.47, 1.34 | 1.3-1.4 | 1.3-1.4 | 25.1 | 24.6 | 28-30 |
| 16 | 1.57, 1.47 | 1.61, 1.41 | 1.3-1.4 | 37.3 | 36.5 | 28-30 |
| 17 | 3.76 | 3.75 | 1.61 | 78.7 | 77.0 | 29.3 |
| 18 | 1.22 | 1.22 | 3.82, 3.58 | 20.2 | 20.5 | 69.5 |

[1]Sophorolipids:
A. *S. bombicola* lactone;
B. *S. bombicola* anionic;
C. *Candida* sp. anionic.

It is understood that the foregoing detailed description is given merely by way of illustration and that modifications and variations may be made therein without departing from the spirit and scope of the invention.

We claim:

1. A method for producing open chain sophorolipids comprising:
   a) inoculating a fermentation medium comprising a carbon source and a lipid, with a *Candida* species selected from the group consisting of *Candida riodocensis* and *Candida* species NRRL Y-27208, and incubating under aerobic conditions and for a period of time effective to produce an open chain sophorolipid in said medium; and
   b) recovering said sophorolipid from said medium.

2. The method of claim 1 wherein said *Candida* species is *Candida* species NRRL Y-27208.

3. The method of claim 1 wherein said recovering comprises separating cells of said *Candida* from said medium and concentrating said sophorolipid.

4. The method of claim 1 wherein said sophorolipid is recovered in substantially pure form and said recovery comprises separating cells of said *Candida* from said medium and at least partially purifying said sophorolipid from said medium.

5. The method of claim 1 wherein said carbon source is effective to support growth of said *Candida*.

6. The method of claim 5 wherein said carbon source comprises glucose, xylose, mannose, sucrose, galactose, mannitol, sorbose, ribose, salicin, arbutin, raffinose, glycerol, erythritol, xylitol, D-glucitol, D-mannitol, D-glucono-1,5-lactone, gluconate, citrate, molasses, hydrolyzed starch, hydrolyzed cellulosic material comprising glucose, corn syrup, beet syrup, sugar cane syrup, sulfite waste liquor, or combinations thereof.

7. The method of claim 6 wherein said carbon source comprises glucose, xylose, mannose, galactose, mannitol, hydrolyzed starch, hydrolyzed cellulosic materiel comprising glucose, or combinations thereof.

8. The method of claim 5 wherein said carbon source comprises a carbohydrate.

9. The method of claim 1 wherein said lipid is effective to support growth of said *Candida*.

10. The method of claim 9 wherein said lipid is selected from the group consisting of free fatty acids or their salts, fatty acid esters, triglycerides, plant oils, animal fats, marine oils, and mixtures thereof.

11. The method of claim 10 wherein said fatty acid is selected from the group consisting of oleic acid, its salts or esters thereof, stearic acid, its salts or esters thereof, palmitic acid, its salts or esters thereof.

12. The method of claim 10 wherein said lipid comprises a plant oil selected from the group consisting of soybean oil, corn oil, olive oil, sunflower seed oil, pennycress oil, high-oleic sunflower seed oil, canola oil, safflower oil, cuphea oil, jojoba oil, coconut oil, and palm kernel oil.

13. The method of claim 12 wherein said lipid comprises a plant oil selected from the group consisting of soybean oil, corn oil and olive oil.

\* \* \* \* \*